United States Patent
Konya et al.

(10) Patent No.: US 8,216,264 B2
(45) Date of Patent: Jul. 10, 2012

(54) DISPOSABLE PUNCTURING DEVICE AND REUSABLE HANDLING DEVICE FOR A PUNCTURING DEVICE

(75) Inventors: Ahmet Konya, Waldsee (DE); Frank Deck, Niederkirchen (DE); Lindley Herpichboehm, Mannheim (DE); Joanna Coleman, South Glamorgan (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 216 days.

(21) Appl. No.: 12/556,039

(22) Filed: Sep. 9, 2009

(65) Prior Publication Data

US 2010/0160941 A1 Jun. 24, 2010

Related U.S. Application Data

(63) Continuation of application No. PCT/EP2008/001560, filed on Feb. 28, 2008.

(30) Foreign Application Priority Data

Mar. 9, 2007 (EP) .................................... 07004860

(51) Int. Cl.
*A61B 5/151* (2006.01)
(52) U.S. Cl. ........................................ 606/182; 600/583
(58) Field of Classification Search .................. 606/167, 606/181–185; 600/583
See application file for complete search history.

(56) References Cited

U.S. PATENT DOCUMENTS

| | | | |
|---|---|---|---|
| 4,230,118 A * | 10/1980 | Holman et al. | 606/182 |
| 4,823,806 A * | 4/1989 | Bajada | 600/557 |
| 5,407,554 A | 4/1995 | Saurer | |
| 5,514,152 A | 5/1996 | Smith | |
| 6,228,100 B1 | 5/2001 | Schraga | |
| 6,589,202 B1 * | 7/2003 | Powell | 604/27 |
| 6,749,618 B2 * | 6/2004 | Levaughn et al. | 606/182 |
| 6,923,764 B2 | 8/2005 | Aceti et al. | |
| 7,138,089 B2 | 11/2006 | Aitken et al. | |
| 7,141,058 B2 * | 11/2006 | Briggs et al. | 606/181 |
| 7,150,755 B2 * | 12/2006 | Levaughn et al. | 606/181 |
| 2002/0120216 A1 | 8/2002 | Fritz et al. | |
| 2003/0211619 A1 | 11/2003 | Olson et al. | |
| 2004/0092994 A1 * | 5/2004 | Briggs et al. | 606/181 |
| 2005/0234494 A1 | 10/2005 | Conway et al. | |
| 2005/0245845 A1 * | 11/2005 | Roe et al. | 600/583 |
| 2009/0030442 A1 | 1/2009 | Potter et al. | |

FOREIGN PATENT DOCUMENTS

| | | |
|---|---|---|
| DE | 2803345 B1 | 6/1979 |
| DE | 19819407 A1 | 11/1999 |
| WO | 02/02180 A2 | 1/2002 |
| WO | 2006/082439 A1 | 8/2006 |

* cited by examiner

*Primary Examiner* — Kathleen Sonnett
(74) *Attorney, Agent, or Firm* — Roche Diagnostics Operations, Inc.

(57) ABSTRACT

A puncturing device includes a band-shaped lancet carrier carrying a plurality of lancets, a transport mechanism for positioning the lancets sequentially in a launch position by moving the band-shaped lancet carrier, a lancet drive for a puncturing movement, the lancet drive comprising an energy storage, a trigger element, and a housing which includes at least two housing parts and encloses the band-shaped lancet carrier and the lancet drive, the housing having an opening against which a body part is pressed for puncturing, wherein the transport mechanism includes at least one part arranged in a fixed position with respect to the housing. The puncturing device is adapted for disposable use in that the housing parts were are irreversibly connected upon enclosing the band-shaped lancet carrier, thereby sealing the band-shaped lancet carrier irremovably in the housing. A reusable handling device can also be used with the puncturing device.

18 Claims, 2 Drawing Sheets

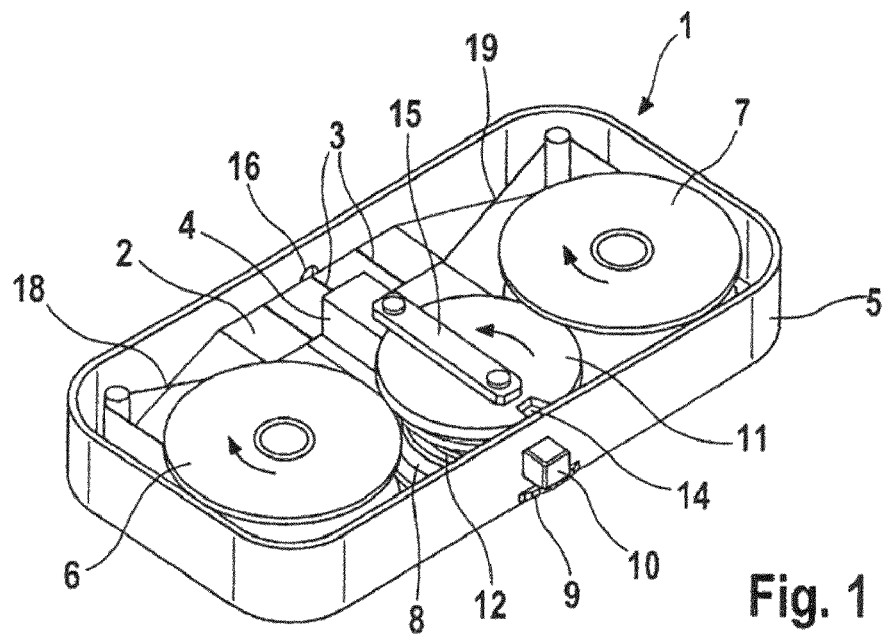
Fig. 1
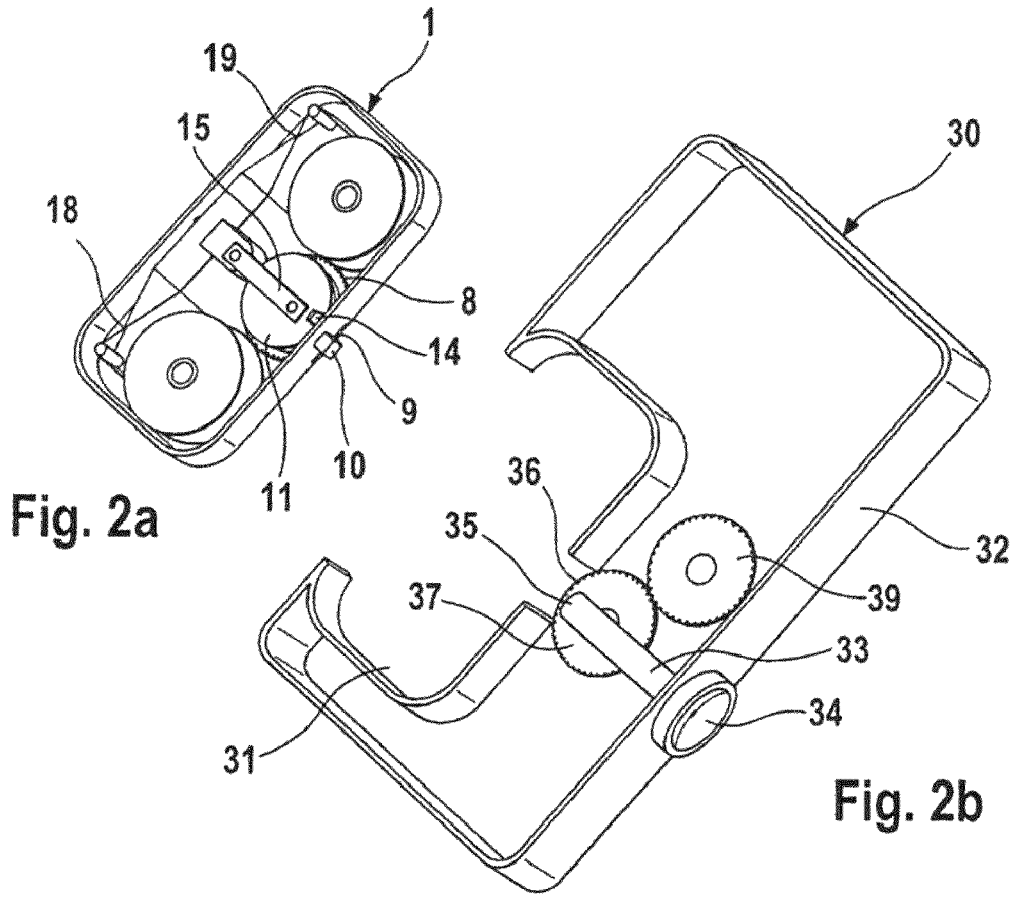
Fig. 2a
Fig. 2b

DISPOSABLE PUNCTURING DEVICE AND REUSABLE HANDLING DEVICE FOR A PUNCTURING DEVICE

CROSS-REFERENCE TO RELATED APPLICATIONS

The present application is being filed as a continuation of International Patent Application No. PCT/EP2008/001560, filed Feb. 28, 2008, which claims priority to European Patent Application No. 07 004 860.8, filed Mar. 9, 2007.

BACKGROUND OF THE INVENTION

The invention relates to a puncturing device comprising a band-shaped lancet carrier carrying a plurality of lancets. Puncturing devices are for example needed by diabetic patients who have to monitor the glucose content of their blood. Modern puncturing devices offer a relatively pain-free way to create a small puncturing which provides body liquid, usually blood or interstitial fluid, for analysis.

Band-shaped lancet carriers of such devices are usually a tape, but may also be a belt or chain. Puncturing devices comprising such a lancet supply provided by a band-shaped lancet carrier carrying a plurality of lancets are known and convenient to use. Once all lancets of a tape have been used, the lancet tape can be exchanged for a new one carrying unused lancets.

Sterile conditions of unused lancets have to be maintained at all times to avoid harmful side effects, like infections, to be caused by the taking of a fluid sample. The design of puncturing devices and lancet tapes must also contribute to the general aim to keep the costs of glucose monitoring as low as possible. Moreover, puncturing devices should have a compact design to ease the burden on patients who have to keep their puncturing device always at hand as they have to use it several times a day.

It is therefore an object of the present invention to show how the costs for monitoring of glucose or other analytes can be lowered. Moreover, it is an object of the present invention to provide a compact puncturing device that can be safely and easily used by a lay operator.

This object is met by a puncturing device as defined by the features of claim 1.

A substantial part of the manufacturing costs of puncturing devices using a lancet tape carrying a plurality of lancets, are caused by the lancet drive and the transport mechanism for moving the lancet into a launch position. As the transport mechanism and the lancet drive can be easily used for hundreds or even thousands of lancing operations, known puncturing devices are designed for exchangeable tapes. For this reason, the housing of such puncturing devices can be reversibly opened and closed for the exchange of a band-shaped lancet carrier.

Although some costs can be saved in this way, the inventors have realized that even larger cost savings can be achieved by a puncturing device which does not allow for an exchange of a band-shaped lancet carrier and is therefore adapted for disposable use. Exchangeable tapes need a separate packaging to maintain sterile conditions of the lancets during storage, transportation and handling. Costs associated with such a packaging can be avoided by a puncturing device according to the invention. Moreover, a puncturing device according to the present invention can be manufactured at lower cost as such parts like lids for reversibly opening and closing a tape compartment are not needed. Hence, a puncturing device according to the present invention provides a way to lower the costs associated with the treatment of diabetes or other diseases which require monitoring of an analyte concentration in blood or interstitial fluid.

A puncturing device according to the present invention has the additional advantages of a very compact design and easier handling, because patients do not have to replace tapes, and improved safety, because any risk of contamination due to handling of lancet tapes can be avoided.

BRIEF SUMMARY OF THE INVENTION

The housing of a puncturing device according to the present invention comprises at least two housing parts between which an irreversible connection is formed upon enclosing the band-shaped lancet carrier thereby enclosing the carrier irremovably in the housing. Within the context of the present invention the terms "irreversible" and "irremovably" mean that the housing cannot be opened nor the tape removed from the housing without destroying the housing.

The at least two parts of the housing may be manufactured as separate pieces which are connected when the band-shaped lancet carrier is enclosed in the housing. It is also possible to manufacture the housing as a single piece which comprises two parts which can be moved in relation to each other, for example by bending along a fold line which connects the parts. Such a housing may be made of plastic and a fold line, along which two housing parts may be pivoted with respect to each other, and may be created simply by a reduced thickness of the material. For example, a housing provided as a single piece may comprise a bottom part and a lid, which is connected to the bottom part along a fold line. In such an embodiment the fold line forms a first connection between the housing parts. To achieve irreversible enclosing of the lancet carrier in such a housing a second and irreversible connection has to be formed upon enclosing the band-shaped lancet carrier, for example along the rim of a lid-part where it touches a bottom-part after closing. Such a second connection may, for example, be achieved by welding, use of an adhesive or positive locking.

As puncturing devices according to the invention can be provided with a very compact design which is very advantageous for travelling, some patients prefer larger devices for home use as larger devices can offer the advantage of easier handling, for example by being provided with larger operation elements. Especially patients whose manual dexterity is impaired by age or disease often prefer larger devices. Manufacturers have therefore often provided different puncturing devices to address the needs of different consumers groups, although the manufacturing of different devices is expensive.

Another aspect of the present invention provides a cost efficient way to meet the demands of different patient groups regarding size and appearance of puncturing devices. This aspect of the invention refers to a reusable handling device for a puncturing device. A reusable handling device according to this aspect of the invention comprises a compartment for holding a puncturing device and a control mechanism which comprises at least one coupling element configured for coupling the control mechanism with an operation element of a puncturing device held in the compartment.

A small puncturing device as defined by the features of claim 1 can be placed in the compartment of such a reusable handling device and actuated via the control mechanism of the handling device. The control mechanism may for example be as simple as a button on the outside of the handling device connected to a pushrod which actuates a button on the outside of the puncturing device. In this way any operation elements of a puncturing device, for example for triggering a lancing operation or activating a transport mechanism to place a fresh lancet in a launch position, can be operated by the handling device.

A reusable handling device can be manufactured at low cost and designed to meet the needs of special patient groups. For example, a handling device with like large operation elements can be provided for elderly patients. A manufacturer can also provide at low cost handling devices with a special appearance appealing to children or the ever changing demands of fashion.

Such a reusable handling device is most advantageous with a puncturing device adapted for disposable use. However, a handling device according to the present invention may also be used with other puncturing devices which may even use a rechargeable lancet supply that may or may not be provided as lancet tapes, e.g. as stack or disk magazines.

Another aspect of the present invention refers to a puncturing device using a covering tape which covers the opening of the device housing against which a body part is pressed for puncturing. Preferably, the covering tape is moved by the transport mechanism of the device together with the band-shaped lancet carrier. Such a covering tape allows a puncturing device to be hygienically used for several patients because the covering tape protects the puncturing device from contamination by body fluids of a patient against whose skin it is pressed.

Although such a covering tape is very advantageous for a puncturing device adapted for disposable use, it may also be used for puncturing devices which may be recharged by exchangeable lancet tapes or lancet magazines. An aspect of the present invention therefore refers to a puncturing device comprising a housing having an opening, against which a body part is pressed for puncturing, and an outward passage and an inward passage for a covering tape, said opening being arranged between the passages, which are adapted for guiding a covering tape from the interior of the housing through the outward passage, across the opening and through the inward passage back into the housing.

If such a puncturing device uses an exchangeable lancet tape, it is advantageous to provide the lancet tape and the covering tape cassette which is configured to be placed in a compartment of the puncturing device. Therefore, an aspect of the present invention refers to a cassette containing a tape carrying a plurality of lancets and on top of that tape a covering tape. Preferably, the covering tape is longer than the lancet carrying tape. For example, a loop of the covering tape may be provided to facilitate covering of the device opening.

Further aspects and advantages of the invention are explained on the bases of exemplary embodiments with reference to the attached figures. Identical and corresponding parts are identified using corresponding reference numerals. It is noted that the scope of the claims is defined by the recitations therein and not by the specific discussion of features and advantages set forth in the present description.

BRIEF DESCRIPTION OF THE SEVERAL VIEWS OF THE DRAWING

FIG. 1 shows an embodiment of a puncturing device in a cut open view;

FIG. 2a illustrates the puncturing device in a second cut open view from below;

FIG. 2b shows a handling device for the puncturing device in a cut open view;

Figure 3:
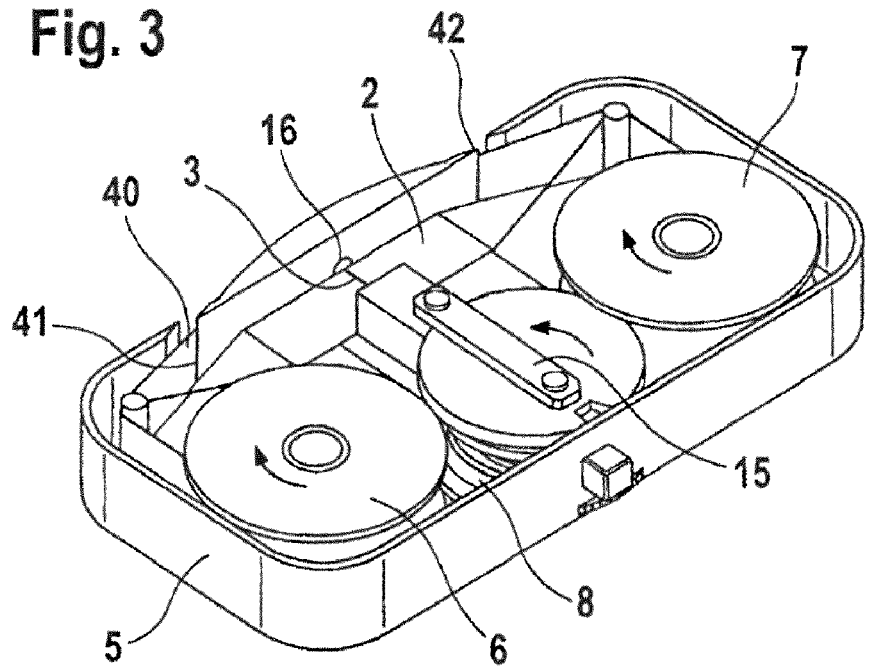
FIG. 3 shows a second embodiment of a puncturing device in a cut open view.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

FIGS. 1 and 2a show a puncturing device 1 adapted for disposable use comprising a tape 2 carrying a plurality of lancets 3, a transport mechanism for positioning the lancets 3 sequentially in a launch position by moving the tape 2, a lancet drive 4 for driving a lancet 3 from the launch position into a puncturing and retraction movement, and a housing 5, in which the tape 2 and the lancet drive 4 are arranged. In FIG. 1, the housing 5 is shown cut open so that components of the device arranged inside the housing 5 can be seen.

The housing 5 comprises two housing parts which are irreversibly connected upon enclosing the tape 2 in the housing 5, thereby sealing the tape 2 irremovably in the housing 5. In the example shown, the first housing part is provided as a bottom part which is closed by a second housing part (not shown) in the form of a lid, after the tape 2, the transport mechanism and the lancet drive 4 have been placed in the bottom part. The bottom part includes a base plate and sidewalls.

Because the housing parts are irreversibly connected, the tape 2 cannot be removed from the housing 5 without destroying the housing 5. An irreversible connection of the housing parts may be achieved by positive locking or, preferably, by a continuous connection as may be achieved by an adhesive or welding. Of course, the housing may constitute more than two irreversibly connected housing parts to achieve the desired result that a user cannot access the interior of the device 1 without destruction.

The transport mechanism of the embodiment shown includes a first reel 6, around which an unused section of the tape 2 is wrapped carrying unused lancets, and a second reel 7 for wrapping used sections of the tape 2 carrying used lancets. The positions of both reels 6, 7 with respect to the housing 5 are fixed. The second reel 7 is coupled to a drive wheel 8 in such a way that a rotation of the drive wheel 8 causes a rotation of the second reel 7. The drive wheel 8 protrudes with a section 9 through an opening of the housing 5. Hence, a user can rotate the drive wheel 8 in order to move the tape 2 and position another lancet 3 in the launch position. In the example shown, the drive wheel 8 is provided as a gearwheel for improved coupling with the second reel 7. The reels 6, 7 and the gear wheel are arranged in a fixed position with respect to the housing 5. Although it is in principle also possible to arrange the transport mechanism on a carriage which is movable with respect to the housing in such a way that during a puncturing movement the carriage moves together with a puncturing lancet 3 in the puncturing direction.

In the example shown, the drive wheel 8 constitutes an operation element for operating the transport mechanism as a user may actuate the drive mechanism via the accessible section 9 of the drive wheel 8. Another operation element 10 for operating the lancet drive is provided as a trigger element protruding through another opening in the housing 5. The trigger element 10 is configured for transmitting a pushing motion onto the lancet drive 4 for triggering a puncturing and retraction movement of a lancet 3.

The lancet drive 4 of the embodiment shown comprises a drive spring 12 as an energy storage for providing energy for the acceleration of the lancets. The drive spring 12 may be made of metal but is preferably made of plastic and may be provided as an elastic plastic element, for example a coil, compressible block or band. Other possible energy storage elements include a battery for an electro-magnetic drive. The drive spring 12 acts between a rotor 11 and the drive wheel 8. One end of the drive spring 12 is attached to the drive wheel 8, and the other end is attached to the rotor 11. In this way, the drive spring 12 is coupled to the transport mechanism in such a way that transportation of a lancet to the launch position causes a tensioning of the drive spring. The drive wheel can turn in one direction only. This may be achieved by a ratchet and pawl mechanism, for example.

The rotor 11 is locked by an interlock (not shown) which engages the recess 14 of the rotor 11. Hence, a rotation of the drive wheel 8 causes tensioning of the drive spring 12. After about one full turn the drive wheel is locked and a fresh lancet is in the launch position. If the interlock of the rotor 11 is then opened by pressing the trigger element 10, the tension of the drive spring 12 will cause the rotor 11 to rotate. The trigger element 10 may be integrated into the transport mechanism in such a way that it is automatically actuated after a fresh lancet is placed in the launch position and the drive spring 12 tensioned.

The rotor 11 is coupled to a conrod 15 for transforming a rotary motion of the rotor 11 into a linear puncturing and retraction motion. The linear motion of the lancet drive 4 will cause a lancet 3 facing the opening 16 of the housing, i.e. the lancet in the launch position, to perform a puncturing and retraction motion, i.e. puncture a finger which is pressed against opening 16.

In order to increase the precision with which a lancet 3 is positioned in the launch position, the tape is provided by mechanical position markers which interact with a position sensor of the transport mechanism to stop a positioning movement of the tape 2 when a lancet 3 has reached the launch position. For example, the tape can be provided with equidistant holes as position markers. Every time such a hole reaches the position sensor (not shown), the drive wheel is locked until the rotor 11 has turned, i.e. the lancet has been used.

The lancet tape 2 of the embodiment shown carries at least 100, preferably at least 200 lancets, especially at least 400 lancets, which may be made of steel, for example by laser cutting or etching. The lancets are arranged side by side on the tape 2 as shown in FIG. 1, although it is also possible to arrange the lancets lengthwise. If the lancets 3 are aligned across the longitudinal direction of the tape 2 as shown in FIG. 1, more lancets may be placed on a tape 2 of a given length.

The breadth of the tape is equal or less than 10 mm, preferably equal or less than 8 mm, especially equal or less than 7 mm. In this way the device can be designed in very compact shape with a thickness of 14 mm or less, preferably 12 mm or less, especially 10 mm or less. For example the dimensions of the device may be 60 mm by 30 mm by 10 mm. The puncturing device 1 fills a volume of less than 50 cm$^3$. It is advantageous if it fills a volume of equal or less than 20 cm$^3$, preferably equal or less than 18 cm$^3$, especially equal or less than 15 cm$^3$.

The device has an approximately cuboid shape. The opening 16 of the housing 5 has a distance from the edges of the housing 5 of 10 mm to 35 mm, preferably 10 mm to 20 mm, especially 13 to 17 mm. In the example shown, the opening 16 is arranged in the middle of a longitudinal side of the device.

The tape 2 is arranged with quarter twists 18, 19 between which the launch position is located. The quarter twists 18, 19 contort the tape 2, which is otherwise arranged parallel to the sidewalls of housing 5, in such a way that lancets in the launch position facing the opening 16 are perpendicular to lancets carried by tape sections wrapped around reel 6 or 7. For this reason the device 1 can be made very flat despite holding a rather long lancet tape with 1000 or more lancets 3. To each of the quarter twists any number of half twists may be added to achieve the same configuration (e.g. ¾ twists), although the necessary space increases accordingly.

Adjustment of the puncturing depth may be provided by movement of the lancet drive 4 in relation to the housing 5 which may be achieved by another gearwheel or a slider protruding out of the housing. Another possibility for an adjustment of the puncturing depth is the use of different sized caps. For example a manufacturer may provide three different plastic caps for three different puncturing depths. Such caps can be provided at low cost and plugged onto the opening 16. Another possibility is to provide a cap which can be screwed onto the opening in such a way that the puncturing depths can be adjusted by turning the cap.

The small and compact design of the puncturing device 1 makes it ideally suited for travelling. However, people whose manual dexterity is impaired by disease or advanced age often prefer a larger device with a larger operation element or operation elements for home use. FIG. 2b shows a reusable handling device 30 for the puncturing device 1 shown in FIGS. 1 and 2a. This reusable handling device 30 facilitates handling of the small puncturing device 1.

The handling device 30 comprises a compartment 31 for holding the puncturing device 1 and a control mechanism comprising a coupling element 33 configured for coupling the control mechanism with the trigger element 10 of the puncturing device 1. The coupling element 33 is provided as a button 34 connected to a push rod 35 which actuates the trigger element 10 when the button 34 is pressed and a puncturing device 1 is held in the compartment 31.

The handling device 30 also comprises a coupling element 36 configured for coupling the control mechanism with the transport mechanism of the puncturing device 1. This coupling element 36 comprises a gearwheel 37 configured to engage the drive wheel 8 of the puncturing device 1. Gearwheel 37 of the handling device 30 can be connected to an electro motor (not shown) which may be used for driving the transport mechanism 6, 7, 8 or tensioning of the drive spring 12. Gearwheel 39 in FIG. 2b symbolizes an electromotor or other mechanism for actuating the drive wheel 8 of the puncturing device 1 via the accessible section 9. A possibility for actuating the drive wheel 8 via the accessible section 9 and thereby to drive the transport mechanism is to make button 34 turnable and coupled to gearwheel 37. In this way, the button may be given a dual function to actuate both the trigger element 10 and the drive wheel 8 of the puncturing device 1 via the accessible section 9.

The compartment 31 of the handling device may have an opening corresponding in size and location to opening 16 of the piercing device 1. Another possibility is to provide compartment 31 with a much larger opening as shown in FIG. 2b, e.g. by removing a section of the side wall of the handling device 30 to provide a window to compartment 31.

As the puncturing device 1 is adapted for disposable use it is most cost efficient to limit its design to the most essential features. The handling device 30 can provide additional features like, for example, signaling means for signaling the impending need to exchange the puncturing device 1 or a counter for informing the user about the number of used lancets or the remaining number of unused lancets in the puncturing device 1. The handling device 30 may also include a pressure sensor for automatically triggering a puncturing movement if the device is pressed with a sufficient force against a body part for gaining example. Moreover, the handling device 30 may provide for an adjustment of the puncturing depths, for example by moving the puncturing device 1 inside the compartment 31 in the piercing direction. Other possible features of the handling device 30 include an integrated measuring device for analyzing samples gained by puncturing or a compartment for storing test elements for analyzing a sample.

The handling device 30 may be designed to meet special customer demands. For example, the handling device 30 may be designed especially for use by medical personnel in a hospital. Advantageous features for such a handling device include an indicator to inform a user in time of the need to exchange the puncturing device, for example, if only ten lancets are left. Another possibility is a handling device for pediatric use. Such a handling device might be given the appearance of a toy to make it more appealing to children. The handling device 30 might also be given additional features like a pocket lamp or a laser pointer. With respect to the ever changing demand of fashion an advantage of the handling device 30 is that it comprises a housing 32 surrounding the puncturing device 1. The housing 32 may be only slightly larger than the puncturing device 1 and be used primarily to change its appearance, e.g. with respect to color.

Figure 4:
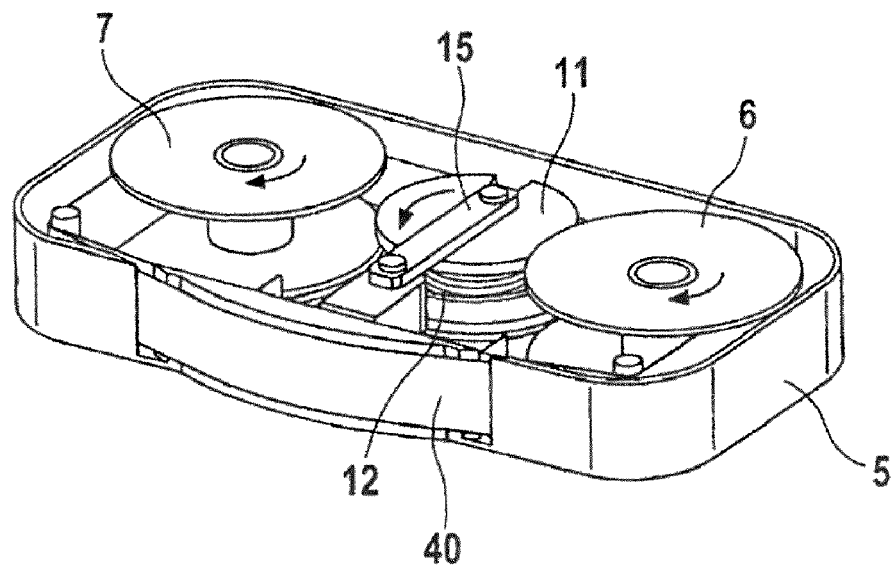
FIG. 4 shows another cut open view of the embodiment shown in FIG. 3.

FIGS. 3 and 4 show another embodiment of a puncturing device 1 adapted for disposable use. This embodiment differs from the embodiment shown in FIGS. 1 and 2a by a covering tape 40 which covers the opening 16 of the housing 5 against which a body part is pressed for puncturing by a lancet 3. The covering tape 40 is moved by the transport mechanism (e.g. reels 6, 7 and drive wheel 8) together with the lancet carrying tape 2. Transport of the lancet tape 2 is thereby directly coupled to the covering tape 40 such that moving the lancet tape 2 causes like movement of the covering tape 40. The lancet carrying tape 2 and the covering tape 40 are both wrapped around the supply reel 6. As sections of the covering tape 2 and the lancet carrying tape 40 are used, they are wrapped around the second reel 7.

The covering tape 40 may for example be made of laminated paper or plastic foil or any other material that can be pierced by a lancet 3. Preferably, the covering tape is transparent to allow a user to see the opening 16 through the covering tape 40. The covering tape 40 serves to prevent contamination of the device 1 by a patient's body fluid. This feature is especially advantageous if the device 1 is to be used for several people, as is usually the case in hospitals.

The housing 5 of the puncturing device 1 shown in FIGS. 3 and 4 has an outward passage 41 and an inward passage 42 for the covering tape 40. The opening 16, against which a body part is pressed for puncturing, is arranged between these passages 41, 42, which are adapted for guiding the covering tape 40 from the interior of the housing 5 through the outward passage 41 across the opening 16 and through in the inward passage 42 back into the housing 5.

The distance between neighboring lancets 3 of the carrier tape 2 is preferably equal or larger than the distance between opening 16 and inward passage 42. In this way the area of the covering tape 40 which has been covering the opening 16 is moved into the device when a new lancet 3 is positioned in the launch position.

In the example shown in FIGS. 3 and 4, the covering tape 40 is provided in the puncturing device 1. Another possibility is to provide the covering tape 40 in the handling device 30.

The advantages of a covering tape 40 may then be used as a feature of the handling device 30 and the puncturing device 1 provided with a very small and compact design. The covering tape 40 may then be much longer than the lancet carrying tape 2 of a puncturing device 1 in order to last for several puncturing devices 1. The covering tape 40 may also be provided as an exchangeable part of the handling device 30, for example provided in a cassette.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A puncturing device comprising:
   a band-shaped lancet carrier carrying a plurality of lancets;
   a transport mechanism for positioning the lancets sequentially in a launch position by moving the band-shaped lancet carrier;
   a lancet drive for accelerating one of the lancets from the launch position for a puncturing movement, the lancet drive comprising an energy storage for providing energy for the acceleration of the lancet, wherein the energy storage includes a drive spring which is coupled to the transport mechanism in such a way that transportation of one of the lancets to the launch position causes a tensioning of the drive spring;
   a trigger element for triggering the lancet drive to release energy from the energy storage to accelerate the lancet for the puncturing movement; and
   a housing which comprises at least two housing parts and encloses the band-shaped lancet carrier and the lancet drive, the housing having an opening against which a body part is pressed for puncturing by the lancet positioned in the launch position, wherein
   the transport mechanism comprises at least one part which is arranged in a fixed position with respect to the housing, and wherein
   the puncturing device is adapted for disposable use in that an irreversible connection between the housing parts is formed and the band-shaped lancet carrier is irremovably enclosed within the housing parts upon assembly of the puncturing device.

2. The device of claim 1, wherein the lancet carrier carries at least 100 lancets.

3. The device of claim 2, wherein the lancet carrier carries at least 200 lancets.

4. The device of claim 1, wherein the transport mechanism comprises a drive wheel which is coupled to a reel for wrapping used sections of the lancet carrier carrying used lancets.

5. The device of claim 4, wherein the drive wheel protrudes through a second opening of the housing.

6. The device of claim 1, wherein the lancet drive comprises a spring-driven rotor and a conrod for transforming a rotary motion of the rotor into a linear puncturing and retraction motion.

7. The device of claim 1, wherein the lancet carrier comprises mechanical position markers which interact with a position sensor of the transport mechanism to stop a positioning movement of the lancet carrier when one of the lancets has reached the launch position.

8. The device of claim 1, wherein the breadth of the lancet carrier is equal to or less than 8 mm.

9. The device of claim 1, wherein the lancet carrier is arranged with two quarter twists between which the launch position is located.

10. The device of claim 1, further comprising a covering tape which covers the opening of the housing against which a body part is pressed for puncturing by one of the lancets.

11. The device of claim 10, wherein the covering tape is moved by the transport mechanism together with the lancet carrier.

12. The device of claim 1, wherein the device has a thickness of 14 mm or less.

13. The device of claim 1, wherein the device has a volume of less than 20 cm$^3$.

14. The device of claim 13, wherein the device has a volume of less than 18 cm$^3$.

15. The device of claim 1, wherein the opening of the housing against which a body part is pressed for puncturing by one of the lancets has a distance from edges of the housing of 10 mm to 20 mm.

16. The device of claim 1, wherein the transport mechanism comprises at least one part which is arranged inside the housing.

17. An assembly comprising a puncturing device and a reusable handling device, wherein
the puncturing device comprises:
   a band-shaped lancet carrier carrying a plurality of lancets;
   a transport mechanism for positioning the lancets sequentially in a launch position by moving the band-shaped lancet carrier;
   a lancet drive for accelerating one of the lancets from the launch position for a puncturing movement, the lancet drive comprising an energy storage for providing energy for the acceleration of the lancet;
   a trigger element for triggering the lancet drive to release energy from the energy storage to accelerate the lancet for the puncturing movement; and
   a housing which comprises at least two housing parts and encloses the band-shaped lancet carrier and the lancet drive, the housing having an opening against which a body part is pressed for puncturing by the lancet positioned in the launch position, wherein
the transport mechanism comprises at least one part which is arranged in a fixed position with respect to the housing, and wherein
the puncturing device is adapted for disposable use in that an irreversible connection between the housing parts is formed and the band-shaped lancet carrier is irremovably enclosed within the housing parts upon assembly of the puncturing device,
and wherein the reusable handling device comprises:
   a compartment for holding the puncturing device; and
   a control mechanism comprising at least one coupling element configured for coupling the control mechanism with the trigger element and/or the transport mechanism held in the compartment such that activation of the control mechanism results in activation of the trigger element and/or the transport mechanism.

18. The assembly of claim 17 wherein the coupling element is configured for coupling the control mechanism with the transport mechanism, wherein the transport mechanism comprises a drive wheel, and wherein the drive wheel protrudes through a second opening of the housing.

* * * * *